US00PP09835P

United States Patent [19]

Spira et al.

[11] Patent Number: Plant 9,835

[45] Date of Patent: Mar. 25, 1997

[54] ASIAN PEAR TREE NAMED 'ASIO 1'

[75] Inventors: Joel S. Spira; Ruth R. Spira, both of Coopersburg; Eugene S. Konno, Germansville; Neil J. Vincent, Quakertown, all of Pa.

[73] Assignee: Subarashii Kudamono Co., Inc., Coopersburg, Pa.

[21] Appl. No.: 531,185

[22] Filed: Sep. 19, 1995

[51] Int. Cl.[6] ..... A01H 5/00

[52] U.S. Cl. ..... Plt./36

[58] Field of Search ..... Plt./36

*Primary Examiner*—James R. Feyrer

*Attorney, Agent, or Firm*—Burns, Doane, Swecker & Mathis

[57] ABSTRACT

A new and distinct variety of Asian Pear, botanically known as *Pyrus pyrifolia* is provided. The new cultivar forms early-ripening medium to large substantially round fruit having a pleasant and refreshing semi-sweet mild flavor. The fruit coloration is bright yellow with prominent tan lenticels. The tree is large and exhibits a vigorous well-branched and spreading growth habit. The leaves are medium green in coloration with moderate venation. Picking of the early-ripening fruit commonly can begin during late August at Coopersburg, Pa., U.S.A. Substantial and consistent fruit crops are formed.

3 Drawing Sheets

SUMMARY OF THE INVENTION

The present invention comprises a new and distinct cultivar of Asian Pear, botanically known as *Pyrus pyrifolia,* and hereinafter is referred to by the cultivar name 'Asio 1'.

The new cultivar germinated from a seed as a distinctive seedling during the summer of 1981 while growing in a test orchard at 1506 Pleasant View Road, Coopersburg, Pa., U.S.A. The new cultivar was discovered among hundreds of seedlings that were produced for test purposes. The seed that produced the new cultivar of the present cultivar was obtained from Japan and was formed on open-pollinated Asian Pear trees. It is impossible to further identify the parent plants of the new cultivar. A single tree of the new cultivar was discovered in the test orchard following selective study and initially was designated No. 209.

Since 1987 the original tree of the new cultivar has annually produced a crop of high quality Asian Pears.

It was found that the new 'Asio 1' cultivar of the present invention:

(a) forms early-ripening mild-flavored substantially round fruit that is yellow with prominent tan lenticels that matures approximately two weeks prior to the 'Twentieth Century' cultivar (non-patented in the United States),
(b) forms a large tree having a vigorous well-branched and spreading growth habit, and
(c) forms medium green leaves with moderate venation.

Asexual reproduction of the new cultivar by budding on 'Bartlett' rootstock at Aspers, Pa., U.S.A. beginning during 1987, has demonstrated that the characteristics of the new cultivar as herein disclosed are firmly fixed and are retained through successive generations of such asexual propagation.

It was found that the 'Asio 1' cultivar flowers concurrently with the 'Twentieth Century' cultivar (non-patented in the United States), but matures approximately two weeks earlier than the 'Twentieth Century' cultivar. The roundish shape of the fruit is similar to that of 'Twentieth Century' cultivar, but commonly exhibits more flavor that the 'Twentieth Century' cultivar.

'Asio 1' has not been observed under all possible environmental conditions to date. Accordingly, it is possible that the phenotype may vary somewhat with variations in the environment, such as temperature, light, day length, contact with pesticides, etc.

The new variety of the present invention will be marketed under the ASAJU trademark.

BRIEF DESCRIPTION OF THE PHOTOGRAPHS

The accompanying photographs show in color as nearly true as it is reasonably possible to make the same in color illustrations of this character the original tree of the new variety as well as plant parts thereof. The well-branched and spreading tree was approximately 13 years of age and was growing on its own roots at 1506 Pleasant View Road, Coopersburg, Pa., U.S.A.

Figure 1:
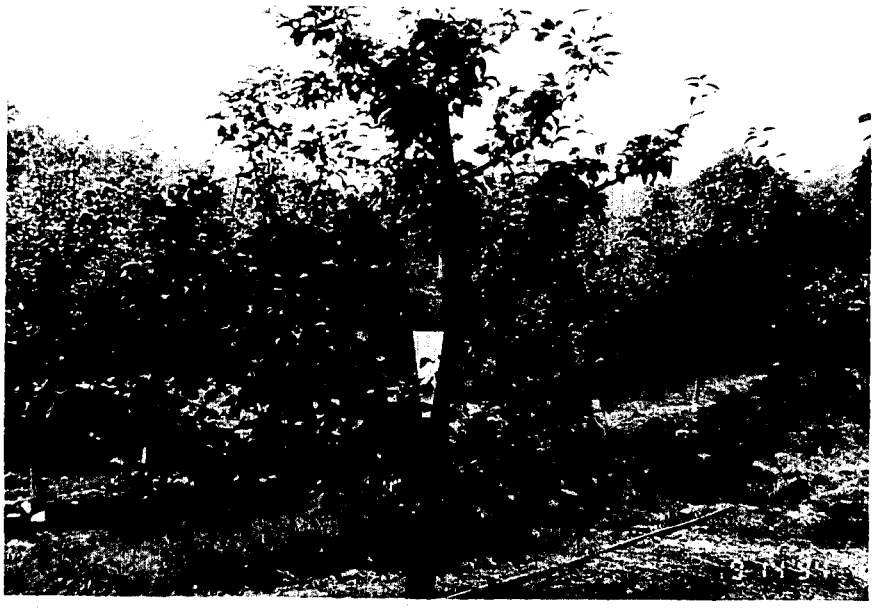
FIG. 1 illustrates the entire tree of the new variety wherein the large tree size and vigorous growth habit are apparent. The photograph was taken on Sep. 14, 1994.
Figure 2:
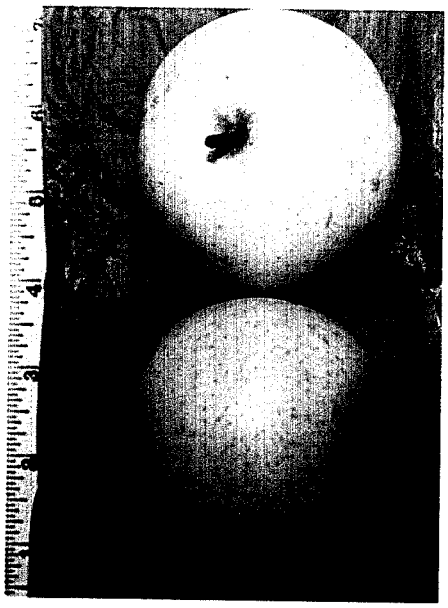
FIG. 2 illustrates specimens of the mature non-russet roundish fruit of the new variety as harvested on Aug. 26, 1995.
Figure 3:
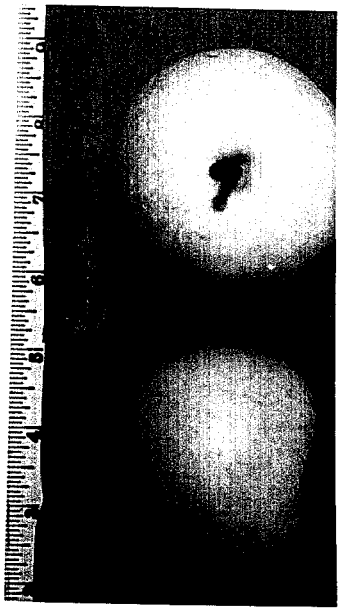

FIG. 3 illustrates additional specimens of the fruit of the new variety as harvested on Aug. 26, 1995. However, in this instance, protective fruit bags manufactured by Hoshino Yoshiten Company of Japan were placed over the fruits when approximately one inch in diameter. Such bags remained in place until the time of harvest and resulted in the formation of fruits having a lighter coloration (as illustrated).

Figure 4:
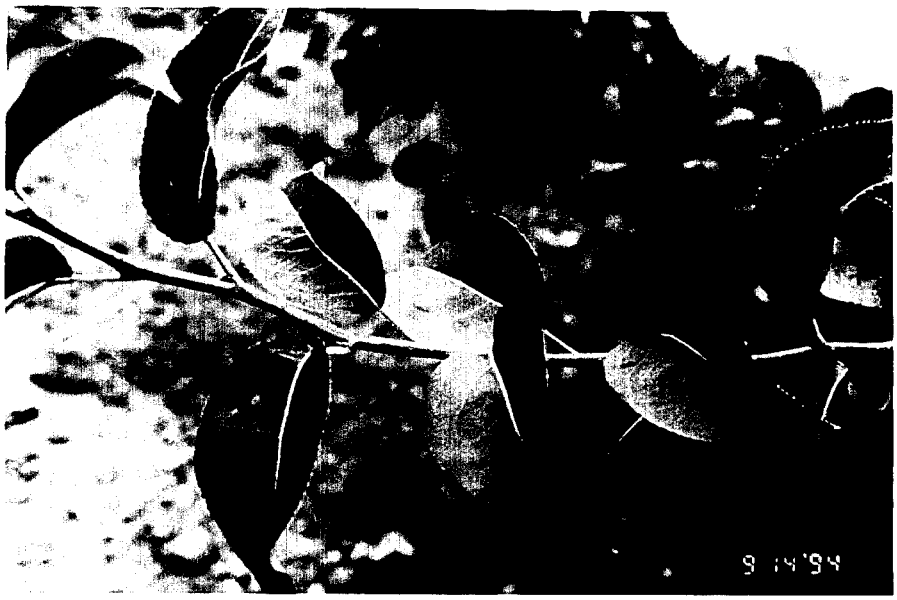

FIG. 4 illustrates a typical limb of the new variety wherein the generally elliptical ovate leaves with serrated edges are apparent. The photograph was taken on Sep. 14, 1994.

Figure 5:
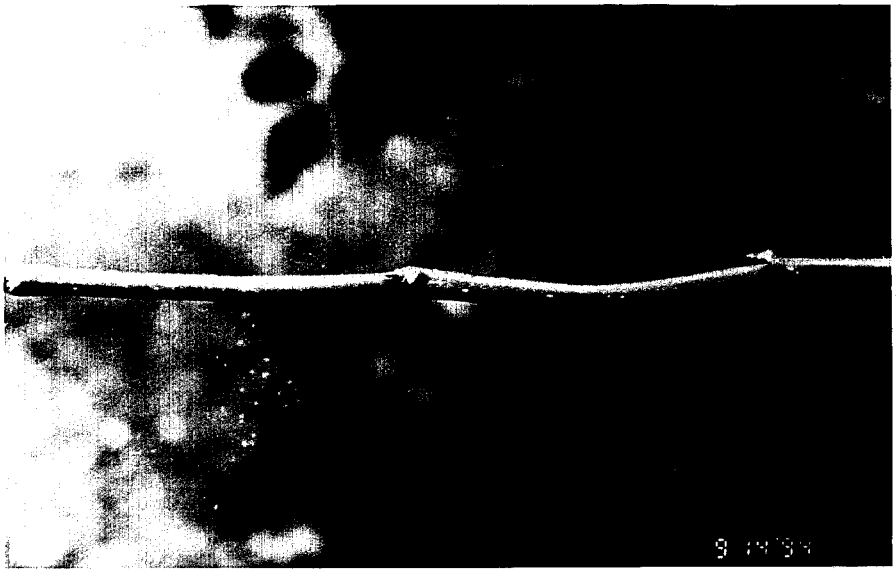

FIG. 5 illustrates a typical limb of the new variety wherein the leaves have been removed so that the smooth appearance of the limb is unobstructed. The photograph was taken on Sep. 14, 1994.

Figure 6:
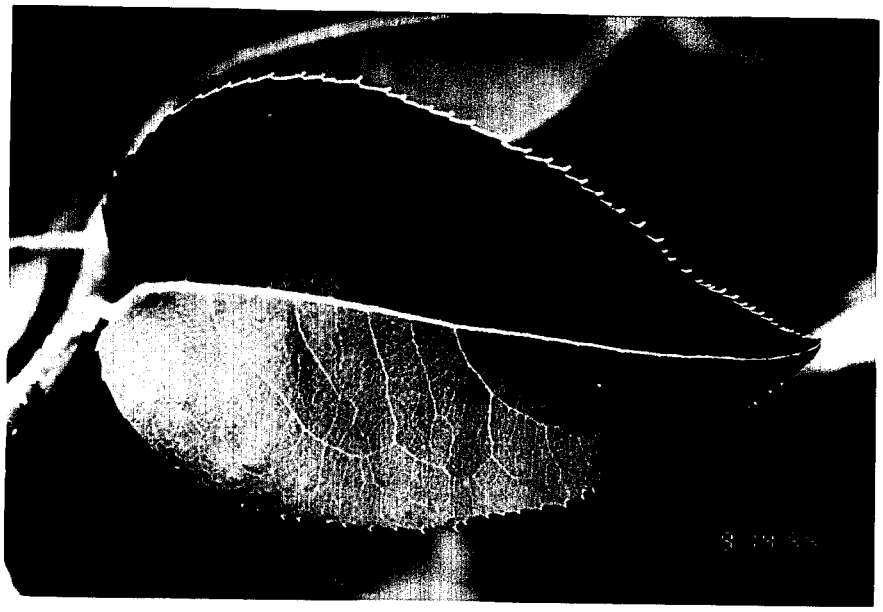

FIG. 6 illustrates a typical elliptical ovate leaflet of the new variety wherein the serration pattern and moderate venation are more readily apparent. The photograph was taken on Sep. 14, 1994.

DETAILED DESCRIPTION

The chart used in the identification of the colors described hereafter is The R.H.S. Colour Chart of The Royal Horticultural Society, London, England. In some instances common color terms are used which are to be accorded their ordinary dictionary significance. The trees described were being grown under standard orchard conditions at Coopersburg, Pa., U.S.A.

Classification:

*Botanical.—Pyrus pyrifolia* (*P. serotina*), cv. *'Asio* 1'.

*Commercial.*—Asian Pear.

Tree:

*Size.*—Large. The original tree at the age of 14 years is approximately 19 feet tall. Two years following the field planting of a tree that was budded 1½ years earlier on 'Bartlett' rootstock, a tree height of approximately 5 feet commonly will be observed. Six years following field planting of a tree that was budded 1½ years earlier on 'Bartlett' rootstock, a tree height of approximately 10 feet commonly will be observed. In the natural state the spread of the tree is approximately equal to the tree height. However, pruning and training can influence the spread to height relationship.

*Growth habit.*—Vigorous, and very strong. For instance, the spreading limbs commonly form more than 18 inches of new growth per year.

*Configuration.*—Spreading.

*Density.*—Dense and well-branched. More specifically, the canopy density can be characterized as being moderately dense, and such density tends to be greater than that of the 'Twentieth Century' cultivar.

*Hardiness.*—Hardy in wood and bud.

*Fruit bearing.*—Productive.

*Bearing habit.*—Annual with the fruit being borne laterally and terminally on second year and older shoots, as well as laterally on spurs.

*Trunk.*—Medium diameter and medium texture.

*Branches.*—Thickness: medium. Bark texture: smooth. Frequency: commonly with profuse branching.

*Branch angles.*—The angles of the main scaffold branches in the natural state commonly are approximately 45 to 60 degrees. When limb spreaders are employed branch angles of approximately 90 degrees can be achieved. The branches of the tree tend to be uncommonly strong based upon the crotch angles of the scaffold branches. Bark texture: smooth (as illustrated). Bark color: chocolate brown on younger wood and charcoal grey on older wood. Internodal length: commonly measure approximately 4 cm. on average. Lenticels: prominent and tan in coloration.

*Leaves.*—Size: large, commonly approximately 12.2 cm. in length on average. Configuration: elliptical ovate. Base: rounded. Apex: acute. Margin: serrulate (as illustrated in FIG. 5). Venation: pinnate, and moderately branched. Thickness: medium. Color upper surface: during a typical growing season is medium green, slightly darker than Green Group 137A and during the fall Yellow-Orange Group 22A. Color under surface: during a typical growing season is silvery green, Green Group 139C, and during the fall near Orange Group 26C. Petiole: short, and approximately 2.5 cm. in length.

*Flowers.*—Season: mid-season, and generally concurrent with the 'Twentieth Century' cultivar. During 1993, the first bud break occurred on Apr. 18th, and full bloom occurred on May 2nd. During 1994, the first bud break occurred on April 17th, and full bloom occurred on May 1st. Size: medium, and commonly approximately 3 cm. in diameter on average. Color: white, White Group 155A. Configuration: The reproductive organs are typical of the species. The flowers generally possess five pistils and bear fruit having five sets of carpels. However, some flowers have been observed that possess six pistils. When six pistils are present, one pistil commonly is substantially shorter than the others, but nevertheless is viable as evidenced by the recovery of some fruit specimens having approximately 11 to 12 seeds. Pollen: viable pollen is produced which has enabled 'Asio 1' to be utilized as the pollen parent in interspecific crosses that have been carried out annually since 1988. When attempts have been made to self-pollinate 'Asio 1', no resulting fruit has set to date. Accordingly, the preliminary indications are that 'Asio 1' may be self-infertile. bearing: commonly in a corymb of 6 to 8 flowers.

*Fruit.*—Season of maturity: early maturing approximately 2 weeks earlier than the 'Twentieth Century' cultivar. During 1993, the first picking was on August 23rd and the last picking was on September 8th. During 1994, the first picking was on August 27th and the last picking was on September 7th. Bearing: most of the fruit is borne laterally on spurs; however, some fruit also can be produced terminally on shoots. Size: medium to large, and commonly approximately 6 to 9 cm. in diameter. The fruit weight commonly ranges from approximately 180 to 300 grams. It is recommended that the fruit be thinned in order to encourage the formation of the larger-sized fruit. Configuration: substantially round. Commonly the fruit width is equal or greater than that of the fruit height. Neck: absent. Stem: medium in length (e.g., approximately 2.5 cm. on average), and thick at the base with thinning towards the point of abscission. Cavity: shallow, acute, and approximately 1.2 cm. in width. Basin: deep and moderately wide (e.g., approximately 2.5 cm.). Calyx: small, recessed, open, and deciduous. Skin: for unbagged fruit the coloration has a bright yellow ground color, approximates Yellow Group 11A, thin, lenticel spots are prominent and tan in color and approach Greyed-Orange Group 165D in coloration. For bagged fruit the skin coloration is significantly lighter, the lentical size tends to be significantly smaller, and the lentical coloration is substantially the same. The fruit cavity typically is russeted. Frequently, but not always the basin is russeted. Flesh: translucent white, very juicy, and crisp. Flavor: semi-sweet (TSS 10 to 13 Brix), delicately mild, and refreshing in taste. Generally exhibits more flavor than the 'Twentieth Century' cultivar. Such fruit flavor is believed to be substantially uniform throughout the fruit Seeds: commonly 6 to 10 per fruit, commonly 1 to 2 per carpel, medium-sized, commonly flattened on one side, and dark brown in coloration. Quality: very good to excellent. Keeping quality: good, can be stored at least 2 months in good condition at 32° F. Fire blight resistance: no inoculations for fire blight screening have been carried out; however, it is believed that at least some resistance to fire blight is being exhibited. For instance, when fire blight strikes have occurred in the orchard where 'Asio 1' was being grown, no fire blight has been observed on 'Asio 1'.

We claim:

1. A new and distinct cultivar as Asian Pear, substantially as illustrated and described, which:

(a) forms early-ripening mild-flavored substantially round fruit that is yellow with prominent tan lenticels that matures approximately two weeks prior to the 'Twentieth Century' cultivar, (b) forms a large tree having a vigorous well-branched and spreading growth habit, and (c) forms medium green leaves with moderate venation.

* * * * *